United States Patent [19]
Scarfone et al.

[11] Patent Number: 5,725,509
[45] Date of Patent: Mar. 10, 1998

[54] AIR INTRODUCTION SYSTEM FOR MEDICAL NEEDLES

[75] Inventors: Frank A. Scarfone, Boca Raton; David Turkel, Miami, both of Fla.; David P. Gordon, Stamford, Conn.

[73] Assignee: Symbiosis Corporation, Miami, Fla.

[21] Appl. No.: 341,528

[22] Filed: Nov. 17, 1994

Related U.S. Application Data

[63] Continuation-in-part of Ser. No. 223,454, Apr. 5, 1994.

[51] Int. Cl.$^6$ .................................................. A61M 5/00
[52] U.S. Cl. .................................................. 604/217
[58] Field of Search ........................ 604/216, 217, 604/75; 128/898; 606/1

[56] References Cited

U.S. PATENT DOCUMENTS

| | | |
|---|---|---|
| 277,568 | 5/1883 | Hendrick . |
| 1,576,128 | 3/1926 | Ballard . |
| 1,824,808 | 9/1931 | Finoley ............................ 604/217 |
| 2,147,158 | 2/1939 | Goldenthal ...................... 604/217 |
| 3,937,219 | 2/1976 | Karakashian . |
| 4,904,240 | 2/1990 | Hoover . |
| 5,139,485 | 8/1992 | Smith et al. . |
| 5,290,257 | 3/1994 | Zhong . |

*Primary Examiner*—William Lewis
*Attorney, Agent, or Firm*—David P. Gordon

[57] ABSTRACT

An air introduction system for a medical needle assembly is provided and includes a flexible bladder, and a male luer assembly with an air valve which is biased to allow air to enter the air introduction system but not to exit. The air introduction system is coupled to a needle assembly which is to be introduced into the epidural space. As the needle traverses the tissue layers overlying the epidural space, and the practitioner applies pressure to the bladder, the practitioner experiences resistance to the forcing of air through the needle assembly. If air is lost from the bladder, the bladder may be refilled by releasing the pressure on it and allowing outside air to enter via the air valve. Once the epidural space is penetrated, air is quickly forced from the bladder through the needle assembly and the practitioner can feel a sudden drop in pressure. To aid in detection, the air introduction system is provided with an air activated sound device situated so as to be exposed to the air flow pushed out of the bladder. With the sound device, an audible warning is provided as the air rushes from the bladder through the needle assembly and into the epidural space.

21 Claims, 4 Drawing Sheets

AIR INTRODUCTION SYSTEM FOR MEDICAL NEEDLES

This application is a continuation-in-part of co-pending application Ser. No. 08/223,454 filed on Apr. 28, 1994 for "Needle Assembly And Methods Useful For Epidural Anesthesia" (Docket No. SYM-126), which is hereby incorporated by reference in its entirety herein.

BACKGROUND OF THE INVENTION

1. Field of the Invention

The present invention relates generally to air introduction systems for medical needle assemblies. The air introduction systems of the invention have particular application to epidural anesthesia, although they are not limited thereto.

2. State of the Art

Epidural anesthesia has gained popularity over the years as being an effective manner of blocking pain without requiring entry to the dura mater of the spinal cord (i.e., a spinal anesthesia). In fact, epidural anesthesia is often the anesthesia of choice in child birth. The preferred surgical procedure for epidural anesthesia starts with the utilization of a 17- or 18-gauge Touhy needle in the lumbar region in order to puncture the skin, and to traverse at least the supraspinous ligament. The Touhy needle is basically a hollow needle having an angled distal tip which is slightly curved (i.e., a Huber point) and a proximal luer fitting, and a solid stylet which sits inside and substantially fills the hollow needle. Once the skin and supraspinous ligament have been traversed by the Touhy needle, the solid stylet is removed from within the hollow needle, and an air filled syringe is coupled to the proximal luer fitting of the hollow needle. With pressure being applied to the plunger of the syringe as well as to the barrel of the syringe, the hollow needle of the Touhy needle is slowly advanced past the interspinous ligament and ligamentum flavum until the needle enters the epidural space between the ligamentum flavum and the dura mater of the spine. Location of the epidural space which is filled with connective tissue, fatty tissue, and blood vessels is indicated by loss of resistance; i.e., less resistance to the injection of air through the needle. In other words, when the pressure applied by the practitioner to the plunger causes the plunger to readily push air through the needle, the practitioner can assume that the epidural space has been reached. Upon entry to the epidural space, the syringe is carefully disconnected from the hollow needle (extreme care being taken to keep the needle in its exact position), and a catheter is threaded through the hollow needle. Because the hollow needle has an angled distal end, upon reaching the distal end of the hollow needle, the catheter is directed into the epidural space which is substantially perpendicular to the direction of the needle. The catheter is advanced only two to three centimeters into the epidural space in order to reduce the likelihood that it might exit through an intervertebral foramen, with resulting inadequate epidural anesthesia. With the catheter in place, a test dose, repeated injections, or a continuous flow of anesthesia may be administered through the catheter.

While the apparatus and methods for administering epidural anesthesia have proved successful over a long period of time, there are several drawbacks to the presently preferred techniques. First, it will be appreciated that even though the Touhy needle is provided with an air filled syringe for detecting when the needle has penetrated the epidural space, the change in resistance of the plunger in the syringe due to the air rushing more easily into the epidural space may not be sufficient to be noticeable to a practitioner. The practitioner therefore runs the risk of overshooting the epidural space and entering the subdural space between the dura mater and the arachnoid mater of the spine, or the subarachnoid space between the arachnoid mater and pia mater of the spine. Such a mistake could result in extreme over-application of anesthesia with a spinal anesthesia and/or possible irreversible paralysis resulting.

Similar complications may also occur where the syringe completely runs out of air due to excessive leakage, thus preventing the practitioner from detecting any change of resistance in the plunger at all. In such a case, in order to avoid the above discussed consequences of overshooting the epidural space, the practitioner must refill the syringe with air in order to properly apply the resistance method. In order to refill the plunger with air, however, the practitioner cannot simply pull the plunger back. To do so would result in the aspiration of various materials from the injection site into the syringe. Rather, the entire needle assembly must be withdrawn completely from the injection site, filled with air, and then reapplied as before. This process may have to be repeated several times before the practitioner succeeds in reaching the epidural space with sufficient air in the syringe to permit detection via the resistance method. Although it is known to have sealed syringes with plungers that have no, or very few air leaks, these syringes are very expensive to manufacture and must still be withdrawn from the sight of injection for air refills if necessary.

SUMMARY OF THE INVENTION

It is therefore an object of the invention to provide an improved air introduction system for a needle assembly.

Another object of the invention is to provide an air introduction system for a needle assembly which is particularly useful in epidural anesthesia and which substantially reduces risks associated with the introduction of an epidural catheter.

It is an additional object of the invention to provide an air introduction system for a needle assembly which provides an audible feedback to the practitioner when air is being forced through the needle assembly.

In accord with these objects which will be discussed in detail below, the air introduction system for a needle assembly of the present invention broadly includes a flexible bulb or bladder having a closed end and an open end, and a male luer adaptor assembly coupled to the open end of the flexible bulb. The male luer adapter assembly includes a male luer and an air valve which is preferably positioned in an air port on the side of the male luer assembly. The valve is biased to allow air to enter the air introduction system but not to exit.

According to the preferred aspects of the invention, the male luer adapter assembly includes proximal exterior threads, distal interior threads, and an air activated sound device. The exterior threads of the male luer adapter assembly are used for positioning and fastening the open end of the flexible bulb to the luer adapter. The interior threads of the male luer adapter are part of a male luer lock which permits the air introduction system to be affixed to a similarly dimensioned female luer lock on a needle assembly. The air activated sound device is preferably centrally situated in the body of the male luer assembly so as to be exposed to the air flow originating from the bulb. The bulb may be blow-molded, or otherwise molded out of any elastic material such as plastic or rubber, and the male luer assembly may be made of any rigid material, preferably plastic. Costs are thus kept to a minimum as the possible presence of minor air leaks is no longer a great concern.

When used with the preferred needle assembly, the male luer of the air introduction system is coupled to a female luer at the proximal end of the needle assembly. As a result, the interior of the air introduction system of the invention is in fluid communication with the interior of the needle assembly and forms an air path therein. This air path permits air injected from the bulb to pass through the needle assembly and into the site of the injection.

According to the method of the invention, while inserting the needle assembly into the epidermis, the practitioner applies pressure to the bulb. Until the needle reaches the epidural space, however, resistance is experienced, and only small amounts of air will escape the needle assembly. Air may also escape the needle and air introduction assembly at other locations depending on the quality and fit of the parts. In the event an excessive loss of air occurs, the practitioner may feel insufficient resistance to properly gage the position of the needle. Using the air introduction system of the invention, the practitioner need only release the applied pressure on the near-empty bulb, and outside air will rush into the air introduction assembly through the open air valve. The practitioner can then continue injecting air through the needle assembly without having to withdraw the needle from the injection site at any time. The bulb may be refilled with air for as many times as is necessary until the needle assembly reaches the epidural space and sufficient air remains available in the bulb for the practitioner to detect the sudden drop in resistance caused by the exiting air. The rushing air will also cause the sound reed in the air introduction system to emit an audible sound.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
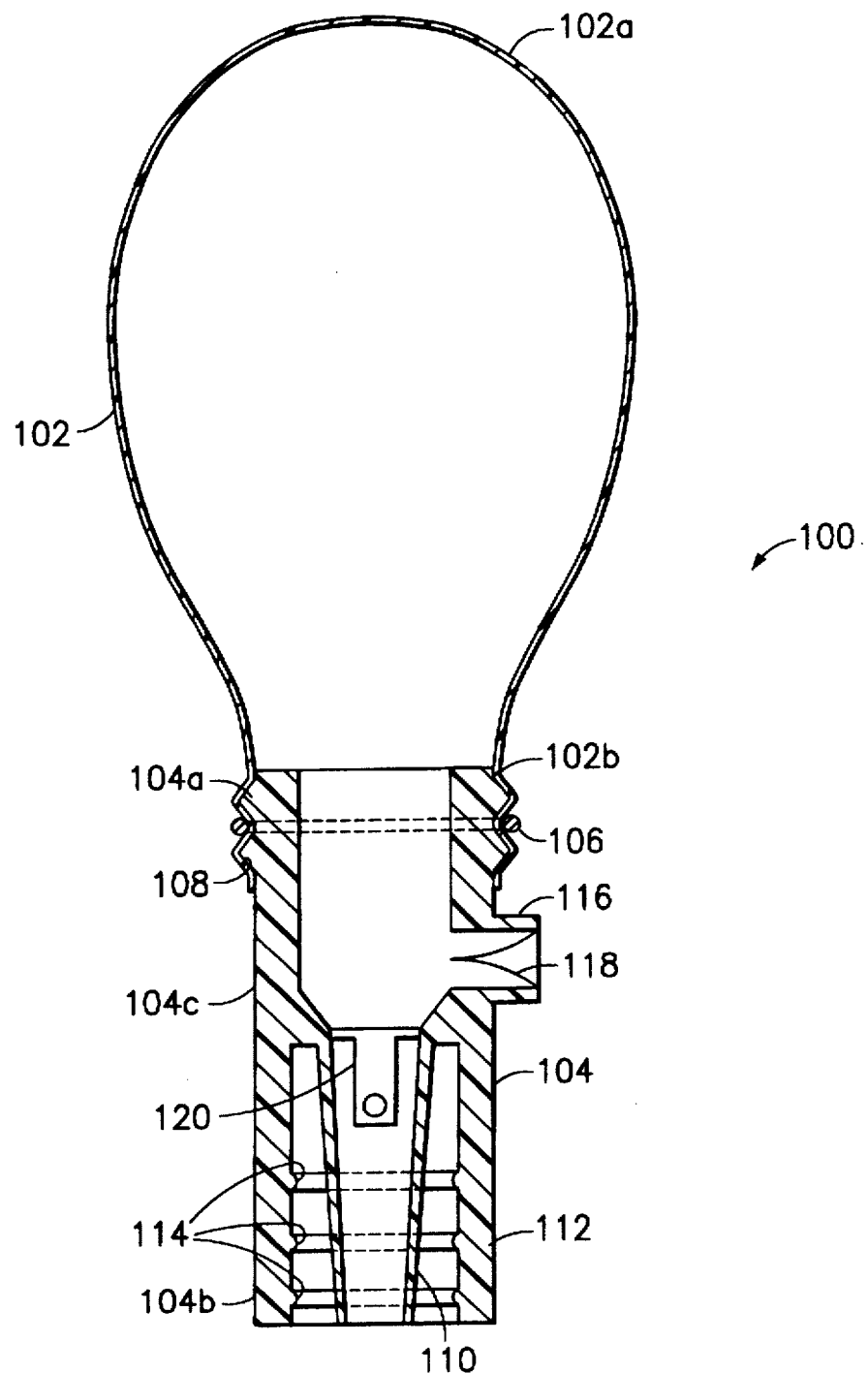
FIG. 1 is a detailed cross sectional view of the air introduction system of the invention.

Turning now to FIG. 1, a detailed cross-sectional view of the air introduction system 100 of the invention is shown. The air introduction system 100 generally includes a flexible bulb 102 having a closed proximal end 102a and an open distal end 102b, a male luer adapter assembly 104 having open proximal and distal ends 104a–b and an elastic ring 106 for affixing the distal end 102b of the bulb 102 to the proximal end 104a of the male luer adapter assembly 104. The male luer adapter assembly 104 further includes exterior threads 108, a male luer 110, a male luer locking mechanism 112 with internal threads 114, an air port 116 containing a duck bill valve 118, and an air activated sound reed 120.

The exterior threads 108 are located at the proximal end 104a of the male luer adapter assembly 104, and are used for positioning and fastening the elastic ring 106 when enclosing the distal end 104a of the bulb 102. The male luer 110 and male luer locking mechanism 112 are situated at the distal end 104b of the male luer assembly 104. It will be appreciated by those skilled in the art that the male luer 110 may be engagedly coupled to a similarly dimensioned female luer 86 (see FIG. 2) which in turn may be attached to a needle assembly 10. In addition, the interior threads 114 of the male luer locking mechanism 112 may be engagedly coupled to the exterior threads 87 of a similarly dimensioned female luer 86 such that the male luer assembly 104 is affixedly locked onto the female luer 86 and the needle assembly 10 as described in further detail below. The air port 116 is situated along the body 104c of the male luer adapter assembly 104 and contains a duck bill valve 118. The valve 118 is sealedly seated within the air port 116 and biased to allow air to enter the air introduction system 100 but not to exit. The air activated sound reed 120 is centrally situated in the body 104c of the male luer adapter assembly 104 so as to be exposed to the air flow originating from the bulb 102 and directed toward the distal end 102b of the male luer adapter assembly 112 as further illustrated below. The bulb 102 may be blow-molded, roto-molded or otherwise molded out of any inexpensive elastic material, such as plastic or rubber. The male luer adapter assembly 104 may be molded out of any inexpensive rigid material, such as polypropylene, polyethylene and the like. The sound reed 120 and air valve 118 may be snap or press fit, or otherwise inserted, located, or seated in the male luer adapter assembly 104. As small air leaks are no longer an important concern with this invention, manufacturing and material costs can be kept to a minimum.

Figure 2:
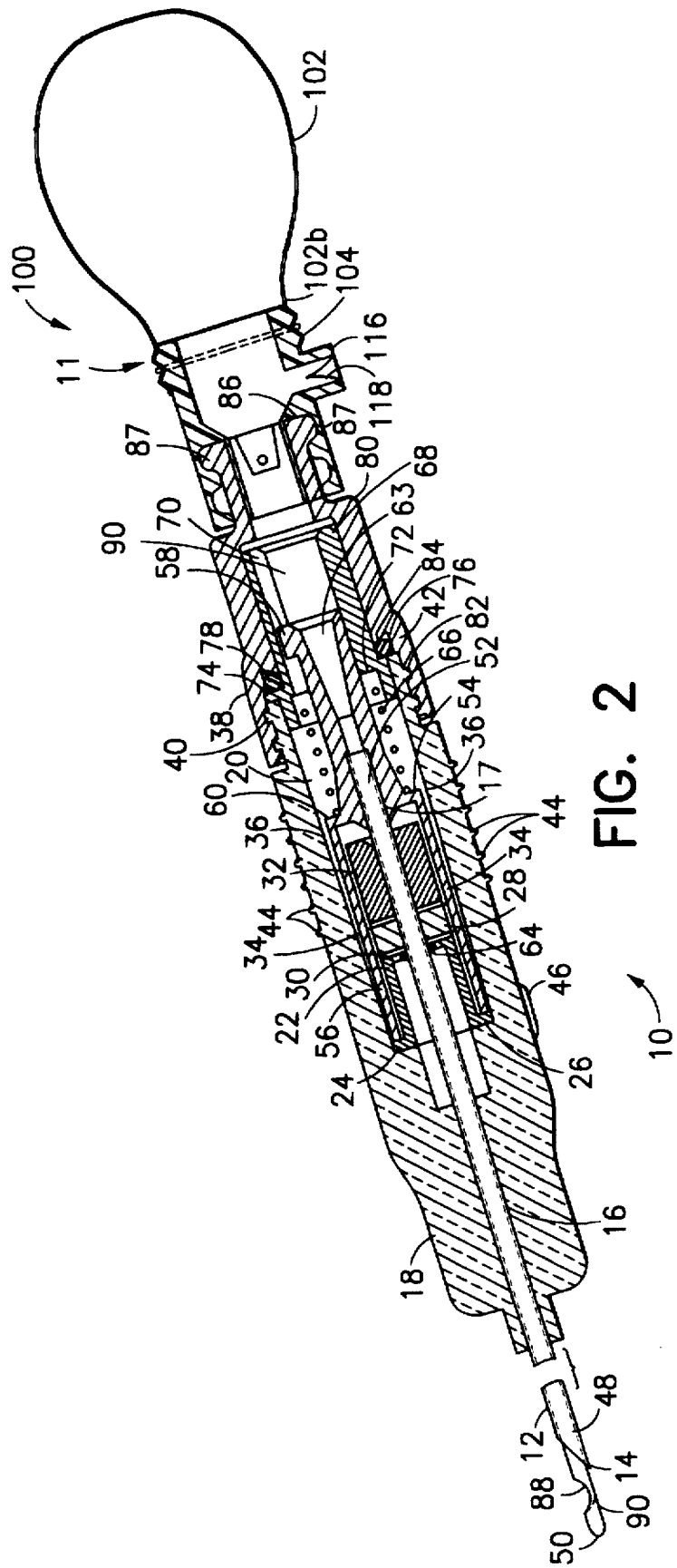
FIG. 2 is a broken longitudinal cross sectional view of the air introduction system of the invention when used in conjunction with a preferred needle assembly.

Referring to FIG. 2, the air introduction system 100 of the invention is shown coupled to the proximal end 11 of the needle assembly 10 described and claimed in previously incorporated parent application Ser. No. 08/223,454. The needle assembly 10 includes a hollow cannula 12 having a sharpened distal end 14 and a proximal portion 16 which is preferably insert molded in a transparent hollow cannula hub 18. The proximal end 17 of the cannula extends approximately half way into the hollow interior 20 of the cannula hub 18. A cylindrical spacer 22 having a distal annular flange 24 is inserted over the proximal end 17 of the cannula 12 until the distal flange 24 abuts the distal annular base 26 of the hollow interior 20 of the cannula hub 18. A first indicator ring 28 having a first pigmentation, preferably green, representing a safety condition, is press fit over the proximal end 17 of the cannula 12 to abut the proximal end 30 of the cylindrical spacer 22 and hold the cylindrical spacer 22 against the distal end 26 of the hollow interior 20 of the cannula hub 18. A second indicator ring 32 having a second pigmentation, preferably pink or red, indicating an unsafe condition is press fit over the proximal end 17 of the cannula 12 and abuts the first indicator ring 28. The spacer 22 and the indicator rings 28, 32 have substantially the same outer diameter and align to form an annular space 34 between them and the interior wall 36 of the hollow cannula hub 18. The proximal end 38 of the cannula base 18 has exterior threads 40 and a lower proximally extending key portion 42. The outer surface of the cannula hub 18 is preferably provided with a ridged finger gripping surface 44 and an indicator marking 46 for indicating the angular position of the cannula hub 18 relative to the longitudinal axis of the cannula 12.

A hollow stylet 48 has a blunt distal end 50 and a proximal end 52 which is insert molded in a hollow stylet hub 54. The stylet 48 extends through the cannula 12 so that the blunt distal end 50 of the stylet 48 extends beyond the sharpened distal end 14 of the cannula 12. The stylet hub 54 has a stepped profile with a wide distal sleeve portion 56 and narrower proximal keyed portion 58 defining an exterior spring seat 60 therebetween. The proximal keyed portion 58 of the stylet hub 54 has a tab key 62 extending radially outward therefrom and an interior fluid and catheter throughbore 63 in fluid communication with the interior of the stylet 48. The distal sleeve portion 56 of the stylet hub 54 is dimensioned to fit in the annular space 34 formed by the cylindrical spacer 22 and indicator rings 28, 32 in the hollow interior 20 of the cannula hub 18. The sleeve portion 56 is substantially opaque except for a transparent window portion 64. A coil spring 66 is placed over the narrower proximal keyed portion 58 and abuts the external spring seat 60. A distally flanged cylindrical member 68 having a keyway 70 and an interior spring seat 72 is inserted into the proximal end 38 of the cannula hub 18 and engages the proximal end of the coil spring 66 with its interior spring seat 72. The distal flange 74 of the cylindrical member 68 is provided with a notch 76 which engages the key portion 42 of the cannula hub 18 and locates the keyway 70 relative to the indicator marking 46 on the surface of the cannula hub 18. A sealing O-ring 78 is placed over the proximal end of the distally flanged cylindrical member 68 and abuts its distal flange 74. A hollow screw cap 80 having distal interior threads 82, an interior seat 84 and a proximal female luer coupling 86 is screwed onto the proximal exterior threads 40 of the cannula hub 18 and engages the proximal side of the O-ring 78 and presses it against the distal flange 74 of the distally flanged cylinder 68.

The distal end of the stylet 48 is provided with a radial opening 88 and an interior deflection surface 90 in the vicinity of the radial opening 88. The purpose of the deflecting surface 90 and the radial opening 88 is so that a catheter which is inserted into the luer coupling will travel freely through the hollow stylet to the deflection surface and be deflected to exit through the radial opening in the distal end of the stylet at an angle relative to the longitudinal axis of the stylet. The radial opening 88 is positioned on the surface of the stylet relative to the key 62 on the stylet hub 54 so that the position of the key 62 indicates the direction of the radial opening 88. Moreover, as mentioned above, the position indicator 46 is located on the cannula hub 18 relative to the cannula hub key 42 which engages the cylindrical member 68 which carries the stylet hub keyway 70. From the foregoing, those skilled in the art will appreciate that the indicator marking 46 on the cannula hub 18 provides an indication of which direction the radial opening 88 in the stylet is facing and thus which direction a catheter will be deflected when a catheter is inserted through the stylet.

The stylet 48 is biased in the distal direction so that its blunt distal end 50 is biased to a position distal of the sharp distal end 14 of the cannula 12 and that the stylet 48 is movable against the force of the coil spring 66 in the proximal direction. The dimensions of the parts described above are such that when the stylet 48 is moved in the proximal direction against the force of the coil spring 66, the sharp distal end 14 of the cannula 12 is exposed so that the cannula may puncture dense tissue. It will also be appreciated that when the stylet 48 is in the position where it extends beyond the distal end 14 of the cannula 12, the window portion 64 of the stylet hub 54 overlies the first indicator ring 28 and that when the stylet 48 is in the position where it exposes the distal end 14 of the cannula 12, the window portion 64 of the stylet hub 54 overlies the second indicator ring 32. It will further be appreciated that a fluid and catheter path is established between the proximal luer coupling 86 and the hollow interior of the stylet 48 through the through bore 63 in the stylet hub 54.

The female luer coupling 86 is preferably a female luer lock and further includes proximal exterior threads 87 which engage the distal interior threads 114 of the male luer adapter assembly 104 of the invention as described above in FIG. 1. As a result, the interior of the air introduction system 100 of the invention is in fluid communication with the catheter throughbore 63 and the interior of the stylet 48 and cannula 12 of the needle assembly 10. It will be appreciated that in this configuration an air path 90 is created along the air introduction system 100 and the needle assembly 10. This air path 90 permits air injected from the bulb 100 to pass from the stylet 48 and cannula 12 into the site of injection. As long as the needle passes the denser area of the interspinous ligament and ligamentum flavum, only small amounts of air will escape out of the stylet and into the surrounding area. Depending on the quality and fit of the various parts, small air leaks may occur at other areas along the needle assembly 10 (see FIGS. 3a–d). It should be noted that no air will escape through the duck bill valve 118 located in the air port 116 of the male luer adapter assembly 104, as the valve 118 is biased to open only when the air pressure outside the air introduction system 100 is greater than the air pressure inside. When this is the case, the outside air will rush into the air introduction apparatus 100 through the open duck bill valve 118 and refill the bulb 102 and male luer adapter assembly 104.

Turning to FIGS. 3a –d, schematic views of the epidural space 304 and needle of the invention 10 are shown. The epidural space 304 is bounded on one side by the ligamentum flavum 302 which lies beneath the epidermis and other tissues 300, and on the other side by the dura mater 306. The epidural space 304 extends narrowly along the axis 307 of the spinal canal (not shown). When the needle of the invention is inserted into the epidermis 300, the stylet 48 is pushed proximally against the coil spring 66 (FIG. 2) and the sharp distal end 14 of the cannula 12 is exposed to pierce through tissue 300. In this position, which is shown schematically in FIG. 3a, the practitioner 308 applies pressure to the bulb causing the air to move in the direction indicated 310. As the distal end 14 of the cannula 12 is moving through the dense ligamentum flavum 302, only a little air escapes 312 from the cannula 12 and stylet 48 into the tissue 302, thus causing the practitioner 308 to experience resistance. Small amounts of air 312a may also escape the needle 10 and air introduction assembly 100 at other areas, depending on the quality and fit of the parts.

Figures 3A, 3B:
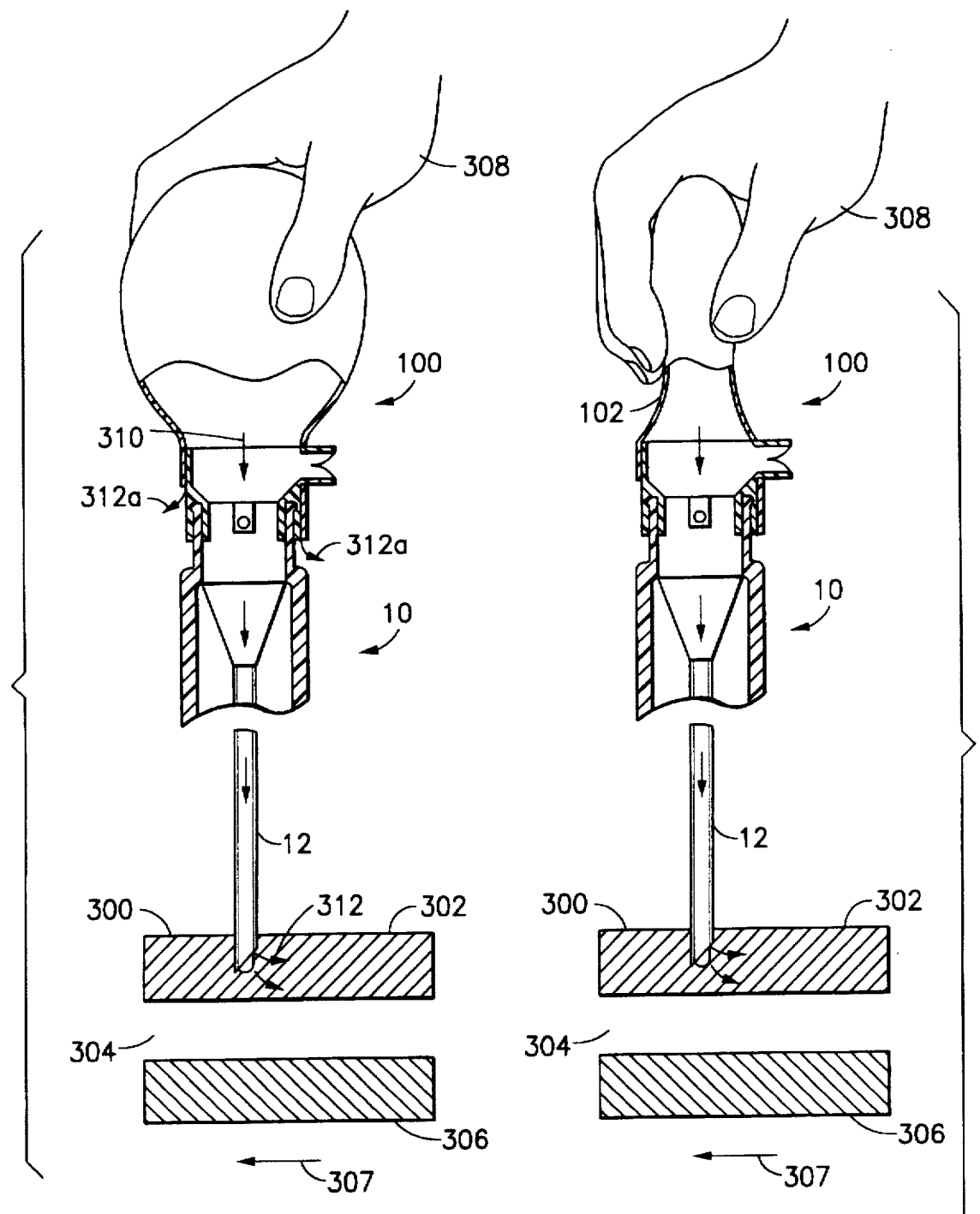
FIG. 3a is a broken longitudinal cross sectional view of the distal end of the air introduction system and needle assembly during a first stage of insertion into the epidural space, when the bulb of the invention contains air.
FIG. 3b is a broken longitudinal cross sectional view of the distal end of the air introduction system and needle assembly during the first stage of insertion into the epidural space, when the bulb of the invention is empty.
Figures 3C, 3D:
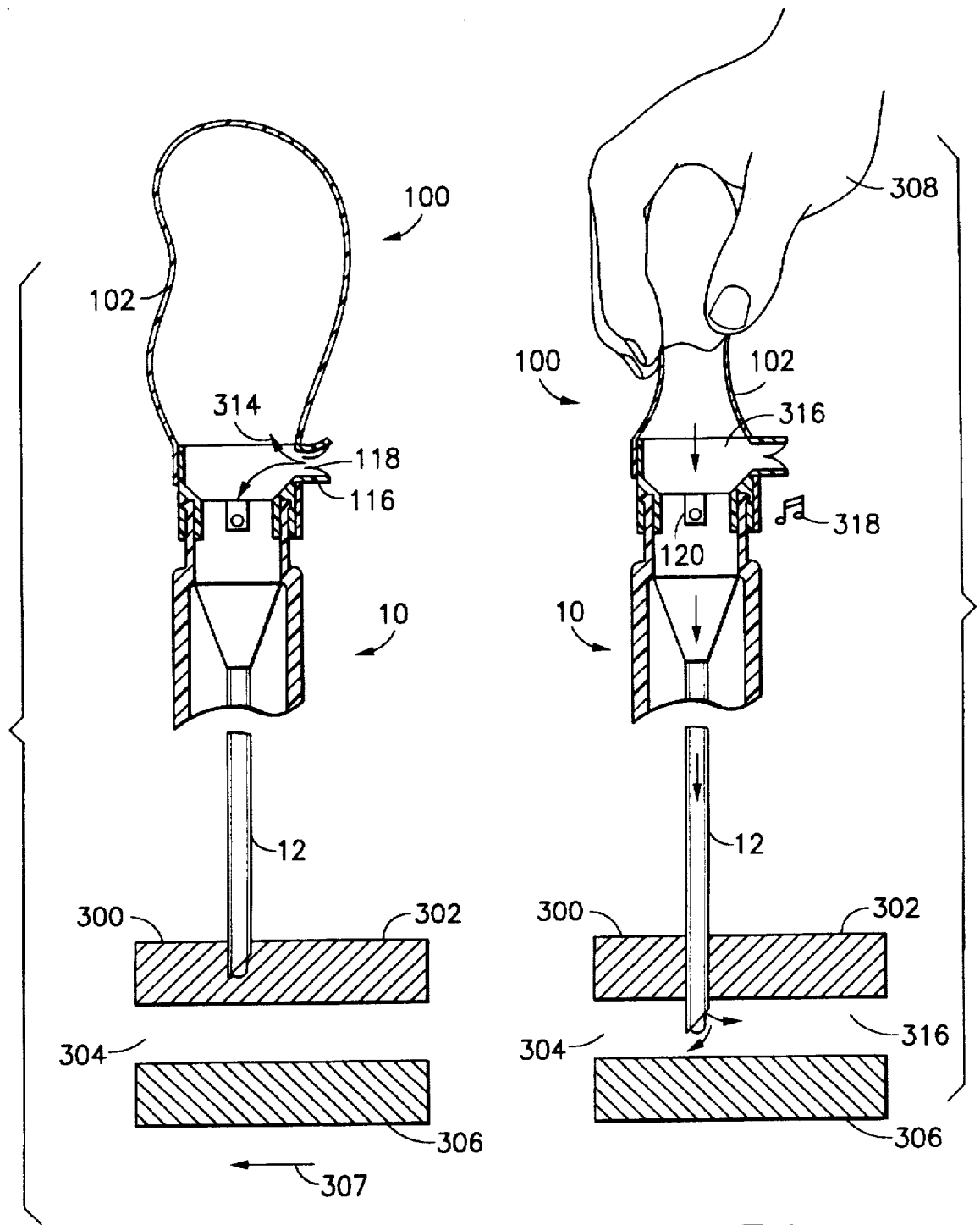
FIG. 3c is a broken longitudinal cross sectional view of the distal end of the air introduction system and needle assembly during the first stage of insertion into the epidural space, when the bulb of the invention is being refilled with air through the air valve.
FIG. 3d is a broken longitudinal cross sectional view of the distal end of the air introduction system and needle assembly during a second stage of insertion into the epidural space, showing the bulb of the invention deflating rapidly and the sound reed emitting an audible sound.

Under optimal conditions, sufficient air remains in the bulb 100 such that when the cannula 12 and stylet 48 finally enter the epidural space 304, the practitioner 308 experiences a noticeable drop in resistance due to the air rushing out of the bulb 100 and needle assembly 10 into the lower density area of the epidural tissue (See FIG. 3d). As noted above, however, various leaks in the needle assembly 10 and prolonged penetration in the dense ligamentum flavum 302 may result in the loss of excessive air within the bulb 102, thus offering the practitioner 308 little or no resistance (see FIG. 3b). In such a case, the practitioner may be unable to determine the position of the cannula 12 and stylet 48 using the resistance method and may need to withdraw the entire needle assembly 10 to refill it with air before reapplying it. Using the air introduction assembly 100 of the invention, however, the practitioner 308 need only release the pressure on the near-empty bulb 102, and outside air 314 will rush into the lower pressure environment of the air introduction assembly 100 through the open duck bill valve 118 (see FIG. 3c). The practitioner 308 can then continue injecting the needle assembly 10 without having to withdraw it from the injection site. The bulb 102 may be refilled with air for as many times as is necessary until the needle assembly 10 reaches the epidural space 304 and sufficient air remains in the bulb 102 for the practitioner 308 to rely on the resistance method. As discussed above, once the cannula 12 and stylet 48 reach the epidural space 304, which is filled with connective tissue, fatty tissue, and blood vessels, the practitioner 308 will experience a sudden drop in resistance due the air 316 rushing out into the epidural space 304 (see FIG. 3d). The rushing air 316 will also cause the sound reed 120 to emit an audible sound 318. The loss in resistance and audible sound 318 will indicate to the practitioner 308 that the cannula 12 and stylet 48 have entered the epidural space 304.

Although only one hand of the practitioner is shown in FIGS. 3a-d to be operating the bulb and needle assembly, it will be appreciated that a second hand placed about the cannula hub 18 is preferred to guide and push the needle assembly 10 into the epidural space 304 in the above mentioned illustration. It is also possible, however, for the practitioner 308 to use only one hand in operating the bulb 102 and needle apparatus 10 such as by grasping the cannula hub 18 by the fingers and holding the bulb 102 in the palm of the hand. In this manner, the practitioner 308 can use the same hand to force the tip of the needle assembly 10 into the patient as well as applying pressure to the bulb 102.

There have been described and illustrated herein several embodiments of an air introduction system for use with a medical needle assembly. While particular embodiments of the invention have been described, it is not intended that the invention be limited thereto, as it is intended that the invention be as broad in scope as the art will allow and that the specification be read likewise. Thus, while particular air introduction systems have been disclosed, it will be appreciated that other air introduction devices could be utilized. For example, while a blow-molded flexible bulb has been disclosed, a squeeze bottle mechanism or other substantially compressible device can also be used. Also, while a particular structure of the male luer adapter assembly has been shown, it will be recognized that the structure of the male luer adapter assembly could be modified in several ways without departing from the spirit of the invention. For example, while an air port has been shown protruding from the male luer adapter assembly walls, the air port may also be flush with these walls and placed elsewhere along the male luer adapter assembly. Moreover, while a particular valve configuration has been disclosed for letting air into the air introduction system, it will be appreciated that other similarly biased valve configurations could be used as well. Furthermore, while the air introduction system and needle assembly have been described as useful in epidural anesthesia, it will be understood that the needle assembly and air introduction system are useful for other medical procedures. It will therefore be appreciated by those skilled in the art that yet other modifications could be made to the provided invention without deviating from its spirit and scope as so claimed.

We claim:

1. An air introduction system for use with a medical needle assembly having an open proximal end, a sharp distal end for piercing the epidermis of a patient, and a proximal female luer means, said system comprising:

a) a flexible air bladder means for introducing air into the open proximal end of the needle assemble, said bladder means having an open distal end attachable to the open proximal end of the needle assemble to provide fluid communication with the open proximal end of the needle assembly; and b) a hollow male luer adapter having an open proximal end, a male luer means at its distal end for coupling to the proximal female luer means, and an air valve means coupled to said flexible air bladder means, and an air valve means for permitting air to enter said bladder means through said air valve means but not to exit through said air valve means, wherein said distal end of said flexible air bladder means is coupled to and in fluid communication with said proximal end of said hollow male luer adapter.

2. An air introduction system according to claim 1, wherein:
   said male luer means comprises a male luer lock.

3. An air introduction system according to claim 1, wherein:
   said air valve means is a duck bill valve.

4. An air introduction system according to claim 1, wherein:
   said proximal end of said hollow male luer adapter has first coupling means for coupling to said flexible air bladder means.

5. An air introduction system according to claim 4, wherein: said first coupling means comprises external threads.

6. An air introduction system for use with a medical needle assembly having an open proximal end, a sharp distal end for piercing the epidermis of a patient, and a proximal female luer means, said system comprising:

a) a flexible air bladder means for introducing air into the open proximal end of the needle assembly, said bladder means having an open distal end attachable to the open proximal end of the needle assembly to provide fluid communication with the open proximal end of the needle assembly;

b) an air valve means coupled to said flexible air bladder means, said air valve means for permitting air to enter said bladder means through said air valve means but not to exit through said air valve means; and c) an air powered sound means for producing an audible sound when a substantial air flow is forced through the needle assembly.

7. An air introduction system according to claim 6, wherein: said air powered sound means is a reed.

8. An air introduction system according to claim 6, further comprising:

d) a hollow male luer adapter having an open proximal end, and a male luer means at its distal end for coupling to the proximal female luer means, wherein said air powered sound means is located in one of said male luer adapter and said flexible air bladder means.

9. An air introduction system according to claim 8, wherein:

said air powered sound means is a reed.

10. A method of introducing a needle assembly through the epidermis of a patient and into a body cavity of a patient, said method comprising:

a) providing a hollow needle assembly with an open sharp distal end and an open proximal end which is coupled to an air introduction system having a valve;

b) piercing the epidermis with the sharp distal end of the needle assembly while applying pressure to said air introduction system;

c) advancing the distal end of the needle assembly toward the body cavity while applying pressure to said air introduction system;

d) refilling said air introduction system with air through said valve without removing said needle assembly from the patient and without detaching said air introduction system from the needle assembly;

f) continuing to advance the distal end of the needle assembly toward the body cavity while applying pressure to said air introduction system until when a sudden drop in resistance in said air introduction system occurs.

11. A method according to claim 10, wherein:

said refilling step comprises releasing pressure on said air introduction system to allow air to enter said air introduction system through said valve.

12. A method of introducing a needle assembly through the epidermis of a patient and into a body cavity of a patient, said method comprising:

a) providing a hollow needle assembly with an open sharp distal end and an open proximal end which is coupled to an air introduction system having a valve and an air powered sound means;

b) piercing the epidermis with the sharp distal end of the needle assembly while applying pressure to said air introduction system;

c) advancing the distal end of the needle assembly toward the body cavity while applying pressure to said air introduction system;

d) refilling said air introduction system with air through the valve without removing said needle assembly from the patient and without detaching said air introduction system from said needle assembly;

f) continuing to advance the distal end of the needle assembly toward the body cavity while applying pressure to said air introduction system until said air powered sound means provides an audible warning that a substantial amount of air is being forced through said needle assembly.

13. A method according to claim 12, wherein:

said refilling step comprises releasing pressure on said air introduction system to allow air to enter said air introduction system through said valve.

14. An air introduction system for use with a medical needle assembly having an open proximal end with a female luer and a sharp distal end for piercing the epidermis of a patient, said system comprising:

a) a flexible air bladder means for introducing air into the open proximal end of the needle assembly, said bladder means having an open distal end attachable to the open proximal end of the needle assembly to provide fluid communication with the open proximal end of the needle assembly;

b) a duck bill valve means coupled to said flexible air bladder means, said duck bill valve means for permitting air to enter said bladder means through said duck bill valve means but not to exit through said duck bill valve means; and c) a hollow male luer adapter having
   i) an open proximal end coupled to and in fluid communication with said open distal end of said flexible air bladder means, and
   ii) a distal end having a male luer coupled to and in fluid communication with the proximal female luer of the needle assembly.

15. A medical needle assembly with an air introduction system comprising:

a) a hollow needle having an open sharp distal end and an open proximal end with a first coupling means;

b) a flexible air bladder means for introducing air into the open proximal end of said hollow needle, said bladder means having an open distal end with second coupling means for removably coupling to said first coupling means to provide fluid communication with said open proximal end of said needle; and c) an air valve means coupled to said flexible air bladder means, said air valve means for permitting air to enter said bladder means through said air valve means but not to exit through said air valve means.

16. A medical needle assembly according to claim 15, further comprising:

d) air powered sound means coupled to said flexible air bladder means for producing an audible sound when a substantial air flow is forced through said needle.

17. A medical needle assembly according to claim 15, wherein:

said first and second coupling means are mating luer connectors.

18. A medical needle assembly according to claim 15, wherein:

said second coupling means includes said air valve means.

19. A medical needle assembly according to claim 15, wherein:

said second coupling means is removably attached to said flexible air bladder means.

20. A medical needle assembly according to claim 19, wherein:

said second coupling means includes said air valve means.

21. A medical needle assembly according to claim 20, further comprising:

d) air powered sound means coupled to said second coupling means for producing an audible sound when a substantial air flow is forced through said needle.

* * * * *